United States Patent
Kim et al.

(10) Patent No.: US 9,569,840 B2
(45) Date of Patent: Feb. 14, 2017

(54) METHOD AND APPARATUS FOR SELECTING SEED AREA FOR TRACKING NERVE FIBERS IN BRAIN

(71) Applicants: SAMSUNG ELECTRONICS CO., LTD., Suwon-si (KR); Industry-University Cooperation Foundation Hanyang University, Seoul (KR)

(72) Inventors: Hei-soog Kim, Anyang-si (KR); Hyug-rae Cho, Seoul (KR); Jun-sung Park, Seoul (KR); Jong-min Lee, Seoul (KR)

(73) Assignees: SAMSUNG ELECTRONICS CO., LTD., Suwon-si (KR); Industry-University Cooperation Foundation Hanyang University, Seoul (KR)

(*) Notice: Subject to any disclaimer, the term of this patent is extended or adjusted under 35 U.S.C. 154(b) by 198 days.

(21) Appl. No.: 14/334,001

(22) Filed: Jul. 17, 2014

(65) Prior Publication Data
US 2015/0023556 A1 Jan. 22, 2015

(30) Foreign Application Priority Data
Jul. 17, 2013 (KR) ........................ 10-2013-0084383

(51) Int. Cl.
*G06K 9/00* (2006.01)
*G06T 7/00* (2006.01)
(Continued)

(52) U.S. Cl.
CPC ............. *G06T 7/0012* (2013.01); *A61B 5/055* (2013.01); *A61B 5/4064* (2013.01);
(Continued)

(58) Field of Classification Search
None
See application file for complete search history.

(56) References Cited

U.S. PATENT DOCUMENTS 8,391,643 B2 * 3/2013 Melbourne ........... G06T 7/0034
382/128
8,593,142 B2 11/2013 Mori et al.
(Continued)

FOREIGN PATENT DOCUMENTS

JP 2003199715 A 7/2003
JP 2004174220 A 6/2004
(Continued)

OTHER PUBLICATIONS

Communication dated Oct. 27, 2014 issued by Korean Intellectual Property Office in counterpart Korean Patent Application No. 10-2013-0084383.
(Continued)

*Primary Examiner* — Shefali Goradia
(74) *Attorney, Agent, or Firm* — Sughrue Mion, PLLC

(57) ABSTRACT

A method for selecting a seed area for tracking nerve fibers in a brain includes performing registration of an atlas which shows a plurality of areas which are included in the brain and image data which relates to the brain, displaying a brain area list with respect to the plurality of areas, selecting a first area from the atlas based on a first user input with respect to the brain area list, extracting an area of the image data which corresponds to the first area, as a seed area, based on a result of the registration, and generating a first image which corresponds to the seed area from the image data, and displaying the generated first image.

17 Claims, 7 Drawing Sheets

(51) Int. Cl.

| | | |
|---|---|---|
| *G06F 3/0484* | (2013.01) | |
| *G06T 3/00* | (2006.01) | |
| *A61B 5/055* | (2006.01) | |
| *G01R 33/56* | (2006.01) | |
| *G01R 33/563* | (2006.01) | |
| *A61B 5/00* | (2006.01) | |

(52) U.S. Cl.
CPC ... *G01R 33/5608* (2013.01); *G01R 33/56341* (2013.01); *G06F 3/04842* (2013.01); *G06T 3/0068* (2013.01); *A61B 2576/026* (2013.01); *G06T 2200/24* (2013.01); *G06T 2207/10092* (2013.01); *G06T 2207/30016* (2013.01)

(56) References Cited

U.S. PATENT DOCUMENTS

| | | | |
|---|---|---|---|
| 2007/0127794 | A1 | 6/2007 | Niogi et al. |
| 2008/0122440 | A1* | 5/2008 | Sakai .............. G01R 33/56341 324/309 |
| 2009/0148012 | A1 | 6/2009 | Altmann et al. |
| 2010/0004527 | A1 | 1/2010 | Dale et al. |
| 2010/0244834 | A1 | 9/2010 | Mori et al. |
| 2011/0199084 | A1 | 8/2011 | Hasan |
| 2013/0102877 | A1* | 4/2013 | Mori .................. A61B 5/055 600/410 |

FOREIGN PATENT DOCUMENTS

| | | |
|---|---|---|
| JP | 2012-034772 A | 2/2012 |
| KR | 101203047 B1 | 11/2012 |
| WO | 2012041364 A1 | 4/2012 |

OTHER PUBLICATIONS

Communication dated Dec. 3, 2014 issued by European Patent Office in counterpart European Patent Application No. 14177390.3.

Clayden et al., "Improved segmentation reproducibility in group tractography using a quantitative tract similarity measure", Neuroimage, Sep. 7, 2006, 12 pages total, vol. 33, No. 2, Academic Press, Orlando, FL, US.

Hai et al, "Diffusion tensor-based fast marching for modeling human brain connectivity network", Computerized Medical Imaging and Graphics, Jul. 19, 2010, pp. 167-178, vol. 35, No. 3, Pergamon Press, New York, NY, US.

Gong et al. "Mapping Anatomical Connectivity Patterns of Human Cerebral Cortex Using In Vivo Diffusion Tensor Imaging Tractography", Jun. 20, 2008, pp. 524-536, vol. 19, No. 3.

Conturo et al., "Tracking neuronal fiber pathways in the living human brain", Proceedings of the National Academy of Sciences, Aug. 1, 1999, pp. 10422-10427, vol. 96, No. 18, National Academy of Sciences, U.S.

Correia et al., "Quantitative tractography metrics of white matter integrity in diffusion-tensor MRI", Neuroimage, Aug. 15, 2008, pp. 568-581, vol. 42, No. 2, Academic Press, Orlando, FL, U.S.

Soldea et al., "Segmentation of Anatomical Structures in Brain MR Images Using Atlases in FSL—A Quantitative Approach", 2010 20th International Conference on Pattern Recognition (ICPR), pp. 2592-2595, IEEE, Piscataway, NJ, USA.

Jenkinson et al., "FSL", Neuroimage, Sep. 16, 2011, pp. 782-790, vol. 62, No. 2.

Wakana et al.; "Fiber Tract-based Atlas of Human White Matter Anatomy" Radiology, Atlas of Human White Matter Anatomy; vol. 230 No. 1; Jan. 2004; 11 pages total.

Wakana et al.; "Reproducibility of quantitative tractography methods applied to cerebral white matter"; Elsevier NeuroImage; vol. 36; 2007, 15 pages total.

Hua et al.; "Tract probability maps in stereotaxic spaces: Analyses of white matter anatomy and tract-specific quantification"; Elsevier; NeuroImage; vol. 39; 2008, 12 pages total.

Communication issued on Apr. 27, 2015 by the Korean Intellectual Property Office in related Application No. 10-2013-0084383.

* cited by examiner

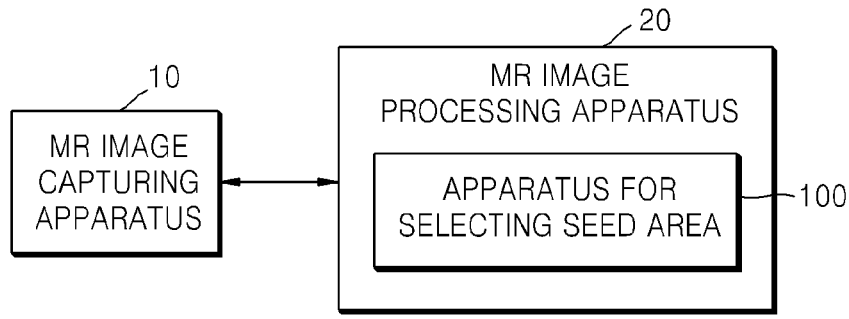
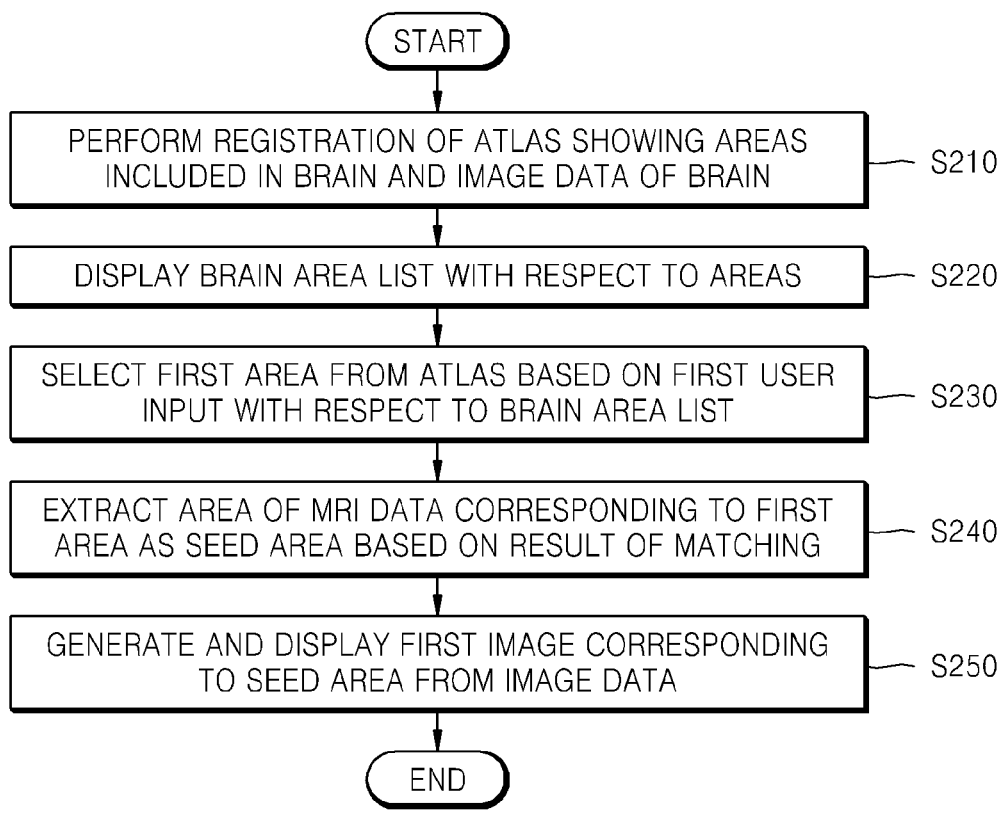

METHOD AND APPARATUS FOR SELECTING SEED AREA FOR TRACKING NERVE FIBERS IN BRAIN

RELATED APPLICATIONS

This application claims priority from Korean Patent Application No. 10-2013-0084383, filed on Jul. 17, 2013, in the Korean Intellectual Property Office, the disclosure of which is incorporated herein by reference in its entirety.

BACKGROUND

1. Field

One or more exemplary embodiments relate to a method and apparatus for selecting a seed area for tracking nerve fibers in a brain, and more particularly, to a method and apparatus for selecting a seed area as an interest area for reconfiguring nerve fibers on an image of a brain which is obtained from magnetic resonance imaging (MRI) data.

2. Description of the Related Art

Magnetic resonance imaging (MRI) is a typical non-invasive brain measuring technique by which a human body is exposed to a uniform magnetic field and a sectional image of the human body is drawn from information that is obtained via nuclear magnetic resonance. Nuclear magnetic resonance signifies that, when a particular high frequency is incident on an atomic nucleus in a state magnetized by an external magnetic field, an atomic nucleus which is in a relatively low energy state absorbs high frequency energy, thereby becoming excited to a relatively high energy state.

According to a diffusion tensor imaging (DTI) technique, which is a type of MRI technique, information which relates to movements of water molecules may be obtained from a resonance signal which is obtained from a human body located in a magnetic field, and a diffusion tensor may be calculated from the obtained information. Then, directivity of nerve fibers in the white matter of a brain is estimated based on the calculated diffusion tensor, and thus the connection of nerve fibers is virtually reconfigured. According to the DTI technique, because an image of neurons of a brain is obtainable, a detailed diagnosis of a brain disease may be obtainable based on the image.

In order to study or clinically use an image of a brain which is obtained by using the DTI technique, a process of searching for tracks which pass particular interest areas within the image of the brain and checking the shapes and trends of corresponding tracks is needed. The interest areas are referred to as seed areas or seed points. The nerve fiber tracks which pass through the seed areas are tracked and may be used for diagnosis of a disease and an operation schedule.

Accordingly, software supporting the DTI technique provides a method of defining a seed area. To this end, a method for receiving a user input which relates to manually drawing a seed area on a 2D image of a brain which has been obtained from DTI data has been used.

However, according to the method of manually defining a seed area, a seed area which is manually drawn by a user must be repeatedly corrected until the desired seed area is correctly represented, and thus, a relatively large amount of time is consumed during the drawing process. Also, in spite of the amount of time spent on manually drawing the desired seed area, the accuracy of a defined seed area may be low.

SUMMARY

One or more exemplary embodiments include a user-friendly method and apparatus for selecting a seed area in order to quickly and accurately define a seed area which is desired by a user.

Additional aspects will be set forth in part in the description which follows and, in part, will be apparent from the description, or may be learned by practice of the presented exemplary embodiments.

According to one or more exemplary embodiments, a method for selecting a seed area for tracking nerve fibers in a brain includes performing a registration of an atlas which shows a plurality of areas which are included in the brain and image data which relates the brain, displaying a brain area list with respect to the plurality of areas, selecting a first area from the atlas based on a first user input with respect to the brain area list, extracting, as the seed area, an area of the image data which corresponds to the first area, based on a result of the performing the registration, and generating a first image which corresponds to the seed area from the image data, and displaying the generated first image.

A plurality of nerve fibers which pass through the seed area may be displayed in the first image.

The atlas may include a white matter atlas.

The image data may include magnetic resonance imaging (MRI) data which is obtainable by using a diffusion tensor imaging (DTI) technique.

The performing the registration of the atlas may include obtaining a fractional anisotropy (FA) map from the image data, and performing a registration of the atlas and the obtained FA map.

The generating and displaying the first image may include sequentially calculating a plurality of nerve fibers which pass through the seed area, and updating the first image based on a result of the calculating, wherein the first image includes image data which corresponds to at least one of the plurality of nerve fibers.

The method may further include displaying a second image, which corresponds to the brain, and which is formed from the image data, and receiving a second user input with respect to the displayed second image, wherein the displaying the brain area list comprises generating and displaying the brain area list with respect to at least one area from among the plurality of areas, which at least one area relates to the received second user input.

The method may further include displaying a second image, which corresponds to the brain, and which is formed from the image data, and receiving a second user input with respect to the displayed second image, wherein the displaying the brain area list comprises generating and displaying the brain area list such that each of the plurality of areas is displayed in the second image, and at least one area from among the plurality of areas, which at least one area relates to the received second user input, is displayed to be different than other areas from among the plurality of areas.

The method may further include displaying a second image, which corresponds to the brain, and which is formed from the image data, receiving a second user input with respect to the brain area list, and displaying at least one area from among the plurality of areas, which displayed at least one are relates to the received second user input, to be different than other areas from among the plurality of areas.

According to one or more exemplary embodiments, an apparatus for selecting a seed area for tracking nerve fibers in a brain includes a data obtainer which is configured for obtaining an atlas which shows a plurality of areas which are included in the brain and image data which relates to the brain, an image registration module which is configured for performing a registration of the obtained atlas, a display device which is configured for displaying a brain area list with respect to the plurality of areas, a user input module which is configured for receiving a first user input with respect to the brain area list, a controller which is configured for selecting a first area from the atlas based on the received first user input, and for extracting, as the seed area, an area of the image data which corresponds to the first area, based on a result of the performed registration, and an image generator which is configured for generating a first image which corresponds to the seed area from the image data, wherein the display device is further configured to display the generated first image.

A plurality of nerve fibers which pass through the seed area may be displayed in the first image.

The atlas may include a white matter atlas.

The image data may include MRI data which is obtainable by using a diffusion tensor imaging (DTI) technique.

The image registration module may be further configured to obtain a fractional anisotropy (FA) map from the image data and to perform a registration of the atlas and the FA map.

The image generator may be further configured to sequentially calculate a plurality of nerve fibers which pass through the seed area and to update the first image based on a result of the calculation, wherein the first image includes image data which corresponds to at least one of the calculated plurality of nerve fibers.

The image generator may be further configured to generate a second image, which corresponds to the brain, and which is formed from the image data. The display device may be further configured to display the generated second image. The user input module may be further configured to receive a second user input with respect to the displayed second image. The brain area list may be generated and displayed with respect to at least one area from among the plurality of areas, which at least one area relates to the received second user input.

The image generator may be further configured to generate a second image, which corresponds to the brain, and which is formed from the image data. The display device may be further configured to display the generated second image. The user input module may be further configured to receive a second user input with respect to the displayed second image. The brain area list may be generated and displayed such that each of the plurality of areas is displayed in the second image, and at least one area from among the plurality of areas, which at least one area relates to the received second user input, is displayed to be different than other areas from among the plurality of areas.

The image generator may be further configured to generate a second image, which corresponds to the brain, and which is formed from the image data. The display device may be further configured to display the generated second image, wherein each of the plurality of areas is displayed in the second image. The controller may be further configured to receive a second user input with respect to the brain area list. The display device may be further configured to display at least one area from among the plurality of areas, which displayed at least one area relates to the received second user input, to be different than other areas from among the plurality of areas.

According to one or more exemplary embodiments, a non-transitory computer readable recording medium having recorded thereon a program, which, when executed by a computer, performs a method for selecting a seed area for tracking nerve fibers in a brain, is provided. The method includes performing a registration of an atlas which shows a plurality of areas which are included in the brain and image data which relates to the brain, displaying a brain area list with respect to the plurality of areas, selecting a first area from the atlas based on a first user input with respect to the brain area list, extracting, as the seed area, an area of the image data which corresponds to the first area, based on a result of the performing the registration, and generating a first image which corresponds to the seed area from the image data, and displaying the generated first image.

BRIEF DESCRIPTION OF THE DRAWINGS

These and/or other aspects will become apparent and more readily appreciated from the following description of exemplary embodiments, taken in conjunction with the accompanying drawings in which:

FIG. 1 is a block diagram which illustrates an MRI system which includes an apparatus for selecting a seed area, according to an exemplary embodiment;

FIG. 2 is a flowchart which illustrates a method for selecting a seed area, according to an exemplary embodiment;

DETAILED DESCRIPTION

Figure 3:
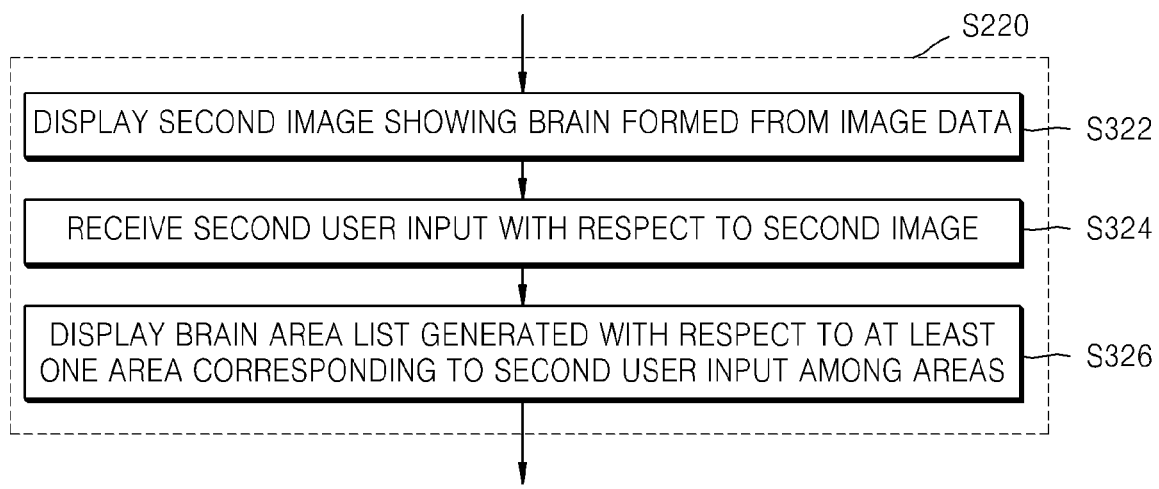
FIG. 3 is a flowchart which illustrates a method for selecting a seed area which comprises displaying a brain area list, according to an exemplary embodiment.

Reference will now be made in detail to exemplary embodiments, examples of which are illustrated in the accompanying drawings, wherein like reference numerals refer to the like elements throughout. In this regard, the present exemplary embodiments may have different forms and should not be construed as being limited to the descriptions set forth herein. Accordingly, the exemplary embodiments are merely described below, by referring to the figures, to explain aspects of the present disclosure. Expressions such as "at least one of," when preceding a list of elements, modify the entire list of elements and do not modify the individual elements of the list.

Unless defined otherwise, all terms used herein including technical or scientific terms have the same meanings as those generally understood by those of ordinary skill in the art to which the present disclosure may pertain. The terms as those defined in generally used dictionaries are construed to have meanings matching that in the context of related technology and, unless clearly defined otherwise, are not construed to be ideally or excessively formal.

When a part may "include" a certain constituent element, unless specified otherwise, it may not be construed to exclude another constituent element but may be construed to further include other constituent elements. The terms such as "~portion", "~unit", "~module", and "~block" stated in the specification may signify a unit to process at least one function or operation and the unit may be embodied by hardware, software, or a combination of hardware and software. Further, as a computer software command to embody the present inventive concept, hardware, software, or a combination of hardware and software may be used instead of a programmed processor/controller. Accordingly, the present inventive concept is not limited by a specific combination of hardware and software.

Throughout the specification, an "object" may be a living thing or a non-living thing that is intended to be displayed in an image. Further, the object may represent a part of a human body or include any section of the human body. For example, the object may represent a brain, but the present inventive concept is not limited thereto. Throughout the specification, a "user" may be any one or more of a doctor, a nurse, a clinical pathologist, a sonographer, a medical image expert, etc. as a medical expert, but the present inventive concept is not limited thereto.

FIG. 1 is a block diagram which illustrates a magnetic resonance imaging (MRI) system which includes an apparatus 100 for selecting a seed area, according to an exemplary embodiment. Referring to FIG. 1, the apparatus 100 for selecting a seed area according to the present exemplary embodiment may be included in an MRI system. The present inventive concept may be widely applied to a medical diagnosis method and apparatus for tracking nerve fibers in a brain based on image data obtained from signals projected onto human tissues by using any one or more of computed tomography (CT), positron emission tomography (PET), ultrasound, etc. in addition to the MRI system of FIG. 1. Although a case in which the apparatus 100 for selecting a seed area according to the present exemplary embodiment is included in an MRI system is described in the following disclosure, the present inventive concept is not limited thereto.

The MRI system may be configured to include a magnetic resonance (MR) image capturing apparatus 10 and an MR image processing apparatus 20. The MR image capturing apparatus 10 may obtain an MR signal from an object (not shown) located inside the MR image capturing apparatus 10, generate image data, and output generated image data to the MR image processing apparatus 20. The MR image processing apparatus 20 may obtain image data from the MR image capturing apparatus 10 and generate a medical image from the obtained data. The MR image processing apparatus 20 may display a generated medical image.

The MR image capturing apparatus 10 and the MR image processing apparatus 20 may be connected to one another in either or both of a wired or wireless manner. Further, unlike the illustration in FIG. 1, the MR image capturing apparatus 10 and the MR image processing apparatus 20 may be incorporated without being physically separated from each other.

The MR image processing apparatus 20 including the apparatus 100 for selecting a seed area according to the present exemplary embodiment may process the image data obtained from the MR image capturing apparatus 10 by using a diffusion tensor imaging (DTI) technique. The MR image processing apparatus 20 may calculate diffusion tensors by obtaining information which relates to movements of water molecules from resonance signals which are obtained from the object. The MR image processing apparatus 20 may generate DTI data based on the calculated diffusion tensor. The MR image processing apparatus 20 may estimate directivity of nerve fibers in the white matter of the brain based on the generated DTI data. Then, the MR image processing apparatus 20 may virtually reconfigure the connection of nerve fibers of a brain based on the estimation.

In order track the nerve fibers based on the generated DTI data, that is, in order to reconfigure the connection of nerve fibers, a process of setting a seed area for the DTI data and calculating the directivity of nerve fibers which pass through the set seed area is required. For example, a user may distinguish a suspected lesion area from normal areas based on a T1 emphasis image and a T2 emphasis image. The user may designate or determine the suspected lesion area as a seed area. The user may input information which relates to a seed area to the MR image processing apparatus 20 by manually drawing a suspected lesion area on a displayed brain image.

However, a suspected lesion area corresponds to a three-dimensional volume. Thus, it is very difficult to define a three-dimensional seed area on a sectional image of a brain. Further, even when a three-dimensional seed area is defined by selecting a two-dimensional section of a suspected lesion area for each of a plurality of sectional images of a brain, it is very difficult to accurately input information which relates to a three-dimensional seed area having a certain shape or a complex shape to the MR image processing apparatus 20. Accordingly, there is a demand for a user-friendly method and apparatus for selecting a seed area by which a user may quickly and accurately define a desired seed area.

The apparatus 100 for selecting a seed area according to the present exemplary embodiment may be configured to segment DTI data based on an atlas of a brain by registration of the atlas and the DTI data. The apparatus 100 for selecting a seed area according to the present exemplary embodiment may provide convenience to a user in selecting a seed area and improve accuracy of a selected seed area. In the following description, a method for selecting a seed area for tracking nerve fibers included in a brain performed by the apparatus 100 for selecting a seed area according to the present exemplary embodiment will be described below with reference to FIG. 2.

FIG. 2 is a flowchart which illustrates a method for selecting a seed area, according to an exemplary embodiment. Referring to FIG. 2, in operation S210, the apparatus 100 for selecting a seed area according to the present exemplary embodiment may perform a registration of image data of a brain and an atlas which shows a plurality of areas which are included in the brain.

The term "atlas" may refer to a brain map which includes anatomical information which relates to a brain. The "anatomical information" may include information which relates to the positions of two or more structures which are respectively arranged at a "predetermined gap", in a "predetermined shape", or at a "predetermined angle", and which are included in the brain. The "structures" may include any one or more from among cells, tissues, nerve fibers, and/or any other suitable structure which may be included in an object.

In the method for selecting a seed area according to the present exemplary embodiment, the atlas may include a white matter atlas. The white matter atlas may be configured based on a plurality of tracks which are formed by grouping a plurality of nerve fibers which are included in the white matter. Because more nerve fibers are distributed in the white matter than in grey matter, use of a white matter atlas may be effective in performing an analysis of nerve fibers based on image data of a brain, such as, for example, the DTI data. The atlas may be generated by statistically analyzing a plurality of brains and modeling the analyzed data. The atlas may be previously stored in or may be input by a user to the apparatus 100 for selecting a seed area according to the present exemplary embodiment.

Further, the image data which is registered with the atlas may include MRI data which is obtainable by using the DTI technique. The apparatus 100 for selecting a seed area according to the present exemplary embodiment may obtain a fractional anisotropy (FA) map from the MRI data and perform a registration of the atlas and the FA map. The FA map is a map which shows a level of diffusion of water molecules that are located in a boundary between the nerve fibers and peripheral tissues. The apparatus 100 for selecting a seed area according to the present exemplary embodiment may use the FA map to track nerve fibers of a brain which pass through a predetermined area.

The image data may be obtained from an image capturing apparatus which is connected to the apparatus 100 for selecting a seed area, or may be previously stored in the apparatus 100 for selecting a seed area. For example, the image data may include MRI data which is obtained from the MR image capturing apparatus 10.

The apparatus 100 for selecting a seed area may segment the image data according to a plurality of areas which are indicated by the atlas by performing a registration of the atlas and the image data. The apparatus 100 for selecting a seed area may perform a registration of the atlas and the image data based on a particular algorithm, such as, for example, any one or more of a linear transformation, a non-linear transformation, and/or any other suitable algorithm, but the present exemplary embodiment is not limited thereto. For the registration of the atlas and the image data, the apparatus 100 for selecting a seed area may perform the registration of the atlas and the image data by comparing the atlas to the image data. Then, the apparatus 100 for selecting a seed area may assign each respective point of the image data, i.e., for example, a pixel or a voxel, to each corresponding area of the atlas.

In operation S220, the apparatus 100 for selecting a seed area according to the present exemplary embodiment may display a brain area list with respect to the areas indicated by the atlas. The brain area list displayed by the apparatus 100 for selecting a seed area may include at least one button which corresponds to all or a part of the areas indicated by the atlas. The at least one button which is included in the brain area list may be marked with the name of an area which corresponds to the at least one button. The at least one button which is included in the brain area list may be marked with a user interface (UI) for receiving a user input for selecting the at least one button.

The brain area list may be previously stored in the apparatus 100 for selecting a seed area, or may be obtained from information which is included in the atlas. In particular, the apparatus 100 for selecting a seed area may store, as default values, information which relates to the areas which are included in a brain that may be selected as a seed area. Further, the apparatus 100 for selecting a seed area may extract information which relates to the areas which are indicated by the atlas from the information which is included in the atlas and generate the brain area list based on the extracted information. The apparatus 100 for selecting a seed area may generate the brain area list such that the areas of a brain which are indicated by the atlas may be registered with the buttons which are included in the brain area list.

In operation S230, the apparatus 100 for selecting a seed area may be configured to select a first area from the atlas, based on a first user input with respect to the brain area list which is displayed on a screen (not shown) in operation S220. The first user input may be received via the UI which is marked on the at least one button that is included in the brain area list.

The first user input with respect to the brain area list may include an input for selecting at least one button from among the buttons which corresponds to the areas of a brain. The first user input may be received via any one or more of a keyboard, a mouse, a trackball, and other similar input devices, and/or received in the form of a touch input to a touch screen. When the first user input is received via a mouse, inputs such as a click, a drag and drop, a mouseover, etc. may be included. For example, the user may click a button which corresponds to an interest area on the brain area list. The apparatus 100 for selecting a seed area may, for example, be configured to select an area of the atlas which corresponds to a clicked button as a first area.

In operation S240, the apparatus 100 for selecting a seed area according to the present exemplary embodiment may extract an area of the image data which corresponds to the first area, based on a result of the registration which is performed in operation S210, and designate the extracted area as a seed area. The apparatus 100 for selecting a seed area may be configured to extract a seed area which corresponds to the first area from the segmented image data. The image data may be segmented according to a plurality of areas which are indicated by the atlas as a result of the registration of the atlas and the image data which is performed in operation S210.

In operation S250, the apparatus 100 for selecting a seed area according to the present exemplary embodiment may generate and display a first image which corresponds to the seed area from the image data. The first image may represent an image of a brain which is generated from the image data and an extracted seed area. The extracted seed area may be displayed in 2 dimensions or 3 dimensions on a 2-dimensional or 3-dimensional image.

The apparatus 100 for selecting a seed area may be configured to extract a plurality of seed areas based on the first user input and to display the extracted seed areas in different colors on the screen. The first image may further include a plurality of nerve fibers which respectively pass through each of the extracted seed areas.

The apparatus 100 for selecting a seed area may be configured to calculate a plurality of nerve fibers which pass through the area which is extracted and designated as a seed area in operation S240, and to generate and display the first image indicating the calculated nerve fibers.

The apparatus 100 for selecting a seed area may be configured to assign various colors to respective nerve fibers based on directivity of each nerve fiber and a seed area which corresponds to each nerve fiber. For instance, the apparatus 100 for selecting a seed area may display the first image showing all of the calculated nerve fibers after the calculation of all nerve fibers which pass through the extracted seed area is completed.

In another instance, the apparatus 100 for selecting a seed area may be configured to sequentially calculate each of the nerve fibers which pass through the extracted seed area and to use a calculation result thereof in order to update the first image so as to display the nerve fibers that are sequentially calculated. In particular, the apparatus 100 for selecting a seed area may be configured to first display the first image showing a part of the nerve fibers which pass through the extracted seed area and then to update the first image in order to provide an image which further shows additionally calculated nerve fibers.

The extracted seed area may include a start point of the calculated nerve fiber, an intermediate point, and an end point. For example, when two or more seed areas are extracted by the apparatus 100 for selecting a seed area, the start point may be included in one of the two or more extracted seed areas, the end point may be included in another of the two or more extracted seed areas, and the apparatus 100 for selecting a seed area may be configured to calculate nerve fibers starting from the start point and ending at the end point.

According to the method for selecting a seed area according to the present exemplary embodiment, because a user may quickly and accurately select the seed area by executing one click of the brain area list, the speed and accuracy of the entire process of tracking nerve fibers which pass through the selected seed area may be improved.

Detailed exemplary embodiments of a method for selecting a seed area according to the present inventive concept will be described with reference to flowcharts in FIGS. 3, 4, and 5. FIG. 3 is a flowchart which illustrates a method for selecting a seed area which comprises displaying a brain area list, according to an exemplary embodiment. Operations S322, S324, and S326 of FIG. 3 may be included in operation S220 of FIG. 2.

In operation S322, the apparatus 100 for selecting a seed area according to the present exemplary embodiment may display a second image showing a brain which is formed from the image data. The second image may include an image showing a section of a brain which is formed by using the DTI technique and/or a 3-dimensional image showing a brain.

In operation S324, the apparatus 100 for selecting a seed area may receive a second user input with respect to the second image displayed in operation S322. The second user input with respect to the second image may include an input for selecting a predetermined area included in the brain. The second user input may be received via any one or more of a keyboard, a mouse, a trackball, and other similar input devices, or received in the form of a touch input to a touch screen. When the second user input is received via a mouse, inputs such as a click, a drag and drop, a mouseover, etc. may be included.

In operation S326, the apparatus 100 for selecting a seed area may generate and display a brain area list with respect to at least one area which corresponds to the second user input from among the areas which are indicated by the atlas. The at least one area which corresponds to the second user input may include at least one area which is included in an area selected by a user via the second user input, an area which includes the selected area, and an area which is included within a predetermined range from the selected area. For example, the user may drag a cursor of a mouse from a predetermined start point to a predetermined end point on the second image. The apparatus 100 for selecting a seed area may be configured to determine that, for example, a circular area which includes a segment connecting the start point and the end point as a diameter is an area which is selected by the user.

The apparatus 100 for selecting a seed area may be configured to search for areas which are included in the area selected by the user from among the areas indicated by the atlas, and to determine searched areas as an area which corresponds to the second user input. The apparatus 100 for selecting a seed area may be configured to generate and display a brain area list with respect to at least one searched area which is determined to be the area which corresponds to the second user input.

In general, the user selects several seed areas from the brain area list and tracks nerve fibers which pass through selected seed areas. However, when a plurality of buttons which correspond to too many areas are listed on the brain area list, the user needs to search through the plurality of buttons one by one to select several desired seed areas. In particular, when a plurality of buttons which correspond to too many areas are listed on the brain area list, the user may spend a lot of time in searching for a button which corresponds to a desired area.

However, the apparatus 100 for selecting a seed area may be configured to display a brain area list in which only those buttons which correspond to some of the areas which are indicated by the atlas in which the user is interested are listed, instead of a brain area list in which all buttons which correspond to all of the areas which are indicated by the atlas are listed.

According to the exemplary embodiment of FIG. 3, the time spent for searching through the brain area list for all areas which are included in the brain may be reduced by displaying the brain area list with respect to some areas in which the user is interested.

Figure 4:
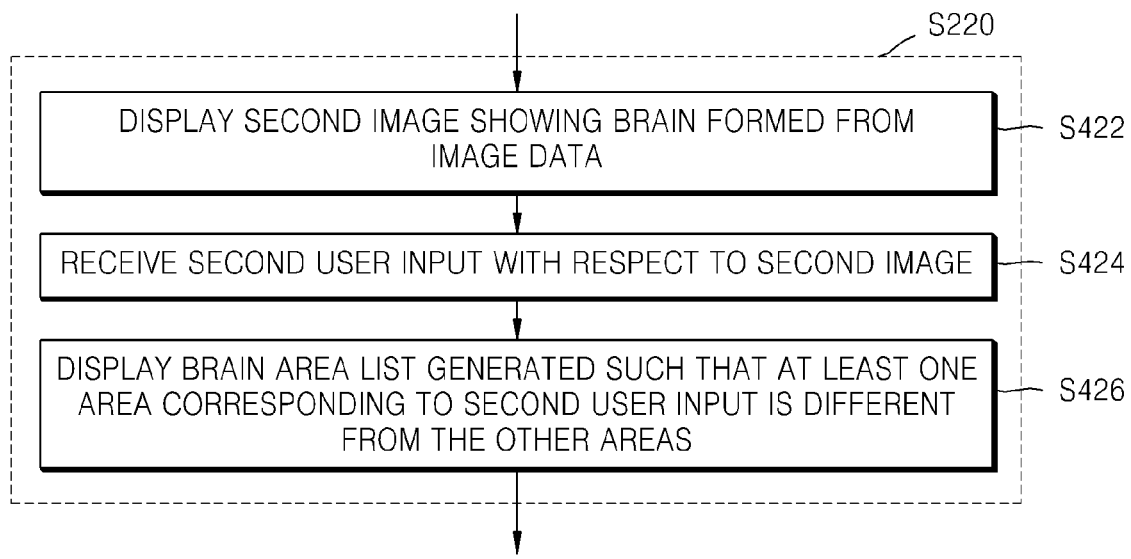
FIG. 4 is a flowchart which illustrates a method for selecting a seed area which comprises displaying a brain area list, according to another exemplary embodiment.

FIG. 4 is a flowchart which illustrates a method for selecting a seed area which comprises displaying a brain area list, according to another exemplary embodiment. Operations S422, S424, and S426 of FIG. 4 may be included in operation S220 of FIG. 2.

In operation S422, the apparatus 100 for selecting a seed area according to the present exemplary embodiment may display the second image showing a brain which is formed from the image data. The second image may be an image showing a section of a brain which is formed by using the DTI technique or a 3-dimensional image showing a brain.

In operation S424, the apparatus 100 for selecting a seed area may receive the second user input with respect to the second image displayed in operation S422. The second user input with respect to the second image may include an input for selecting a predetermined area which is included in the brain. The second user input may be received via any one or more of a keyboard, a mouse, a trackball, and other similar input devices, or received in the form of a touch input to a touch screen. When the second user input is received via a mouse, inputs such as a click, a drag and drop, a mouseover, etc. may be included.

In operation S426, the apparatus 100 for selecting a seed area may generate and display a brain area list such that, from among the areas which are indicated by the atlas, at least one area which corresponds to the second user input received in operation S424 is different from the other areas which do not correspond thereto. The at least one area which corresponds to the second user input may include at least one of an area which is included in an area selected by a user via the second user input, an area which includes the selected area, and an area which is included within a predetermined range from the selected area. For example, the user may locate a cursor of a mouse at a predetermined position on the second image and may perform a click motion. The apparatus 100 for selecting a seed area may be configured to determine that, for example, an area which surrounds the predetermined position corresponds to an area which is selected by the user.

The apparatus 100 for selecting a seed area may be configured to search for the area which is selected by the user from among the areas which are indicated by the atlas, and to determine a searched area as an area which corresponds to the second user input. With respect to the areas which are indicated by the atlas, the apparatus 100 for selecting a seed area may be configured to display, on the brain area list, buttons which correspond to some areas in which the user is interested to be different from buttons which correspond to the other areas. According to the present exemplary embodiment, the buttons which correspond to the other areas in which the user is interested may be displayed to be different from other buttons in terms of shape, color, and brightness. For example, the apparatus 100 for selecting a seed area may be configured to display the buttons which correspond to the second user input such that those buttons which correspond to the second user input are highlighted on the brain area list.

In general, the user selects several seed areas from the brain area list and tracks nerve fibers which pass through the selected seed areas. However, when a plurality of buttons which correspond to too many areas are displayed in the brain area list, the user needs to search through the plurality of buttons one by one in order to select several desired seed areas. Accordingly, the user may spend a lot of time in searching for a button which corresponds to a desired area.

According to the exemplary embodiment of FIG. 4, the time spent for searching through the brain area list for an area which is desired by the user may be reduced by displaying buttons which correspond to areas in which the user is interested such that those buttons which correspond to the second user input are highlighted on the brain area list.

Figure 5:
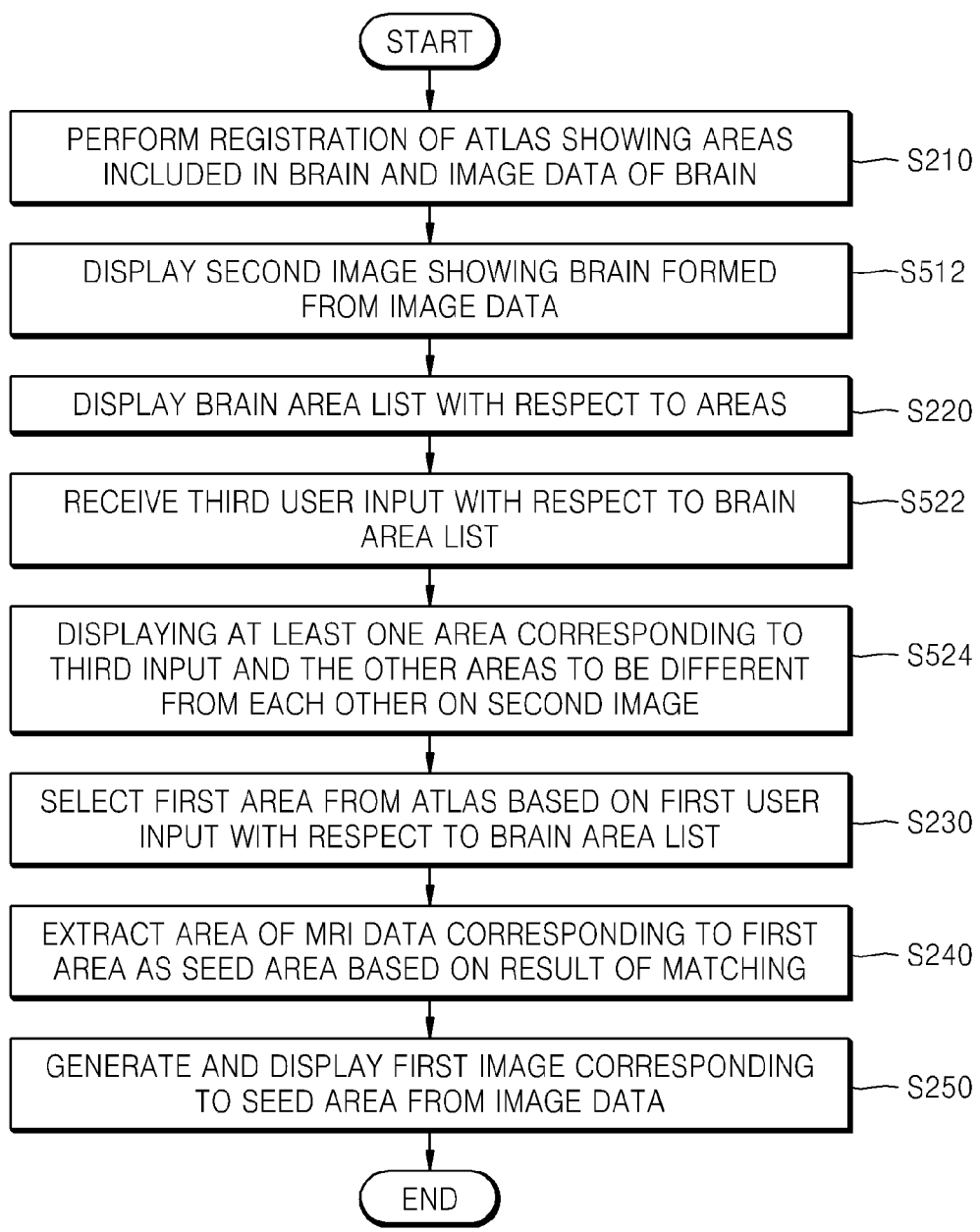
FIG. 5 is a flowchart which illustrates a method for selecting a seed area, according to another exemplary embodiment.

FIG. 5 is a flowchart which illustrates a method for selecting a seed area, according to another exemplary embodiment. Because operations S210, S220, S230, S240, and S250 of FIG. 5 correspond to operations S210, S220, S230, S240, and S250 of FIG. 2, redundant descriptions thereof will be omitted herein.

In operation S512, the apparatus 100 for selecting a seed area according to the present exemplary embodiment may display the second image showing a brain which is formed from the image data. In operation S522, the apparatus 100 for selecting a seed area may receive a third user input with respect to the brain area list which is displayed in operation S220.

The third user input with respect to the brain area list may include an input for selecting at least one button from among the buttons which correspond to the areas of a brain. The third user input may be received via any one or more of a keyboard, a mouse, a trackball, and other similar input devices, or the third user input may be received in the form of a touch input to a touch screen. When the third user input is received via a mouse, inputs such as a click, a drag and drop, a mouseover, etc. may be included.

The third user input with respect to the brain area list may include an input of a different type from the first user input for selecting a seed area. For example, the third user input may include an input of placing a cursor over one of the buttons listed on the brain area list, i.e., a mouseover, which is different from the first user input of clicking a button.

In operation S524, the apparatus 100 for selecting a seed area may display the areas indicated by the atlas such that at least one area which corresponds to the third user input is different from the other areas on the second image.

The at least one area which corresponds to the third user input may include at least one of an area which is included in an area selected by a user via the third user input, an area which includes the selected area, and an area which is included within a predetermined range from the selected area. For example, the user may perform a mouseover motion in order to locate a cursor of a mouse over a button which corresponds to an interest area in the brain area list. The apparatus 100 for selecting a seed area may be configured to determine that, for example, the area which corresponds to the button above which the cursor of a mouse is located corresponds to an area which is selected by the user. When a mouseover input is received from the user, the apparatus 100 for selecting a seed area may be configured to display the at least one area which is selected by the user to be different from the other areas in terms of shape, color, brightness, etc.

In general, the user selects several seed areas from the brain area list and tracks nerve fibers which pass through the selected seed areas. However, when a plurality of buttons which correspond to too many areas are listed on the brain area list, the user needs to search through the plurality of buttons one by one in order to select several desired seed areas. Accordingly, the user may spend a lot of time in searching for a button which corresponds to a desired area.

According to the exemplary embodiment of FIG. 5, as the area which corresponds to the third user input with respect to the brain area list is displayed on the second image of the brain, the user may easily recognize the name of a brain area which corresponds to a predetermined button on the brain area list and the position of a corresponding area.

Accordingly, according to the exemplary embodiment of FIG. 5, because the user quickly searches for an interest area on the brain area list, the time necessary for selecting a seed area may be reduced.

Figure 6:
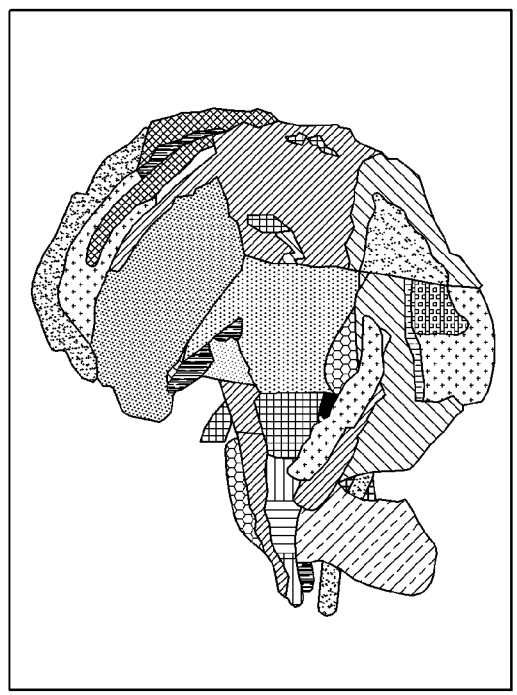
FIG. 6 is a view which illustrates a white matter atlas which shows a plurality of areas which are included in white matter, according to an exemplary embodiment.

FIG. 6 is a view which illustrates a white matter atlas which shows a plurality of areas that are included in white matter, according to an exemplary embodiment. Referring to FIG. 6, the apparatus 100 for selecting a seed area according to the present exemplary embodiment may be configured to select a seed area by using an atlas that segments a brain into 3-dimensional areas. The atlas illustrated in FIG. 6 indicates a plurality of areas which are formed by grouping nerve fibers which are included in the white matter. The apparatus 100 for selecting a seed area may be configured to segment the image data into a plurality of areas by performing a registration of the atlas and the image data.

Figure 7:
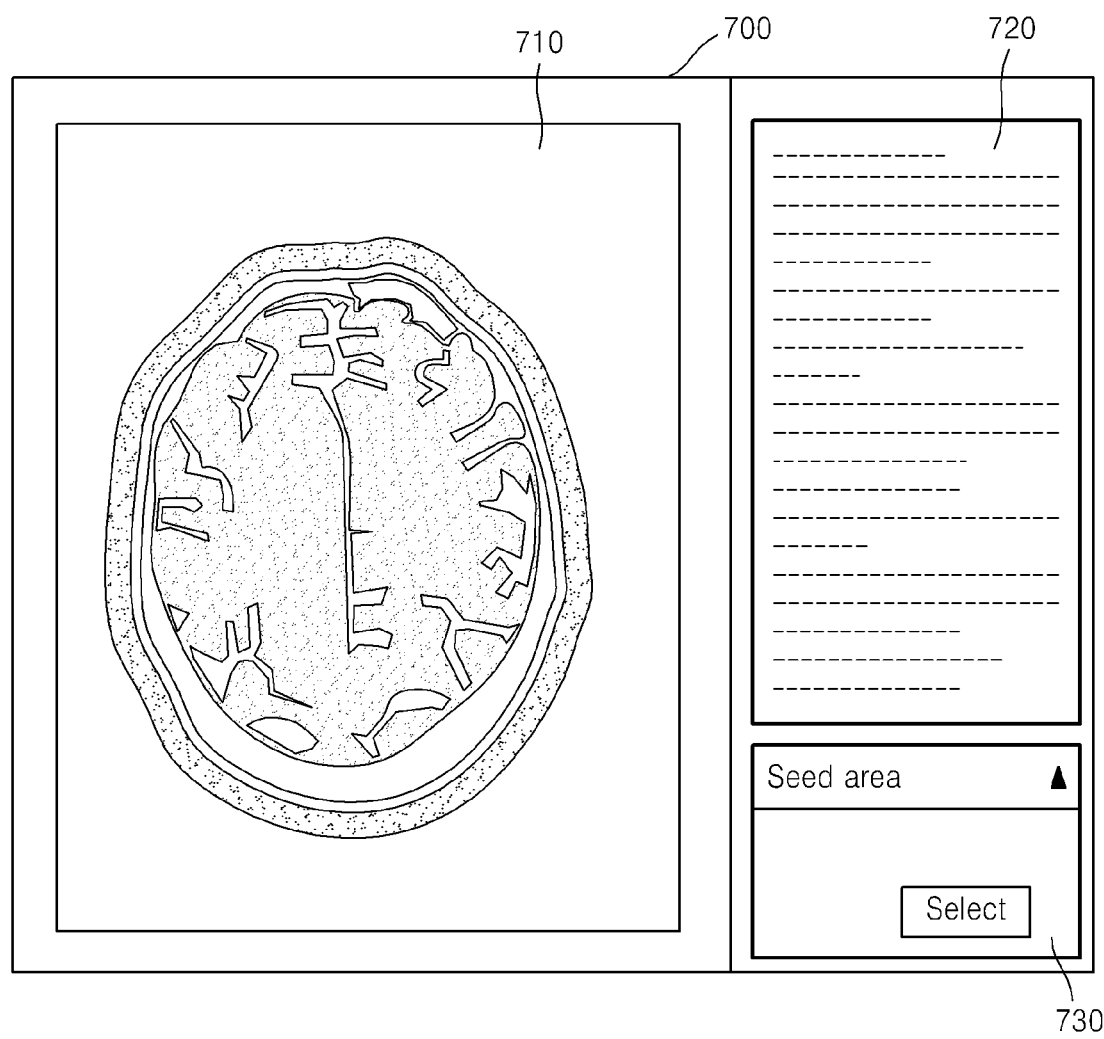
FIG. 7 illustrates an example of a screen which is displayed by an apparatus for selecting a seed area, according to an exemplary embodiment.

FIG. 7 illustrates an example of a screen which is displayed by the apparatus 100 for selecting a seed area, according to an exemplary embodiment. For example, the apparatus 100 for selecting a seed area according to the present exemplary embodiment may output a screen 700 as illustrated in FIG. 7.

An image which shows a brain may be displayed in an area 710. Examples of the image which is displayed in the area 710 may include at least one of an image which is generated from the image data of a brain, an image which is generated from the atlas of a brain, and an image which is generated from a result of a registration of the image data of a brain and the atlas of a brain.

A user interface (UI) which relates to state information and function settings which are needed for obtaining and processing medial image data may be displayed in an area 720. The UI which is displayed in the area 720 may include at least one of, for example, a UI for selecting whether to correct an error of MR data which is generated by an eddy current, a UI for selecting a type of a DTI map, a UI for selecting an algorithm to be used for tractography, and a UI for selecting a color to indicate nerve fibers which are displayed on the screen 700.

The DTI map to be displayed by the apparatus 100 for selecting a seed area may include at least one of a fractional anisotropy (FA) map, a mean diffusivity (MD) map, an apparent diffusion coefficient (ADC) map, and a color map.

A UI for receiving a user input when executing a method for selecting a seed area according to the present exemplary embodiment may be displayed in an area 730. For example, as illustrated in FIG. 7, when the user selects a button which is labeled "Select" and displayed in the area 730, the apparatus 100 for selecting a seed area may be configured to display, on the screen, a brain area list based on the atlas which shows a plurality of areas of a brain.

Figure 8:
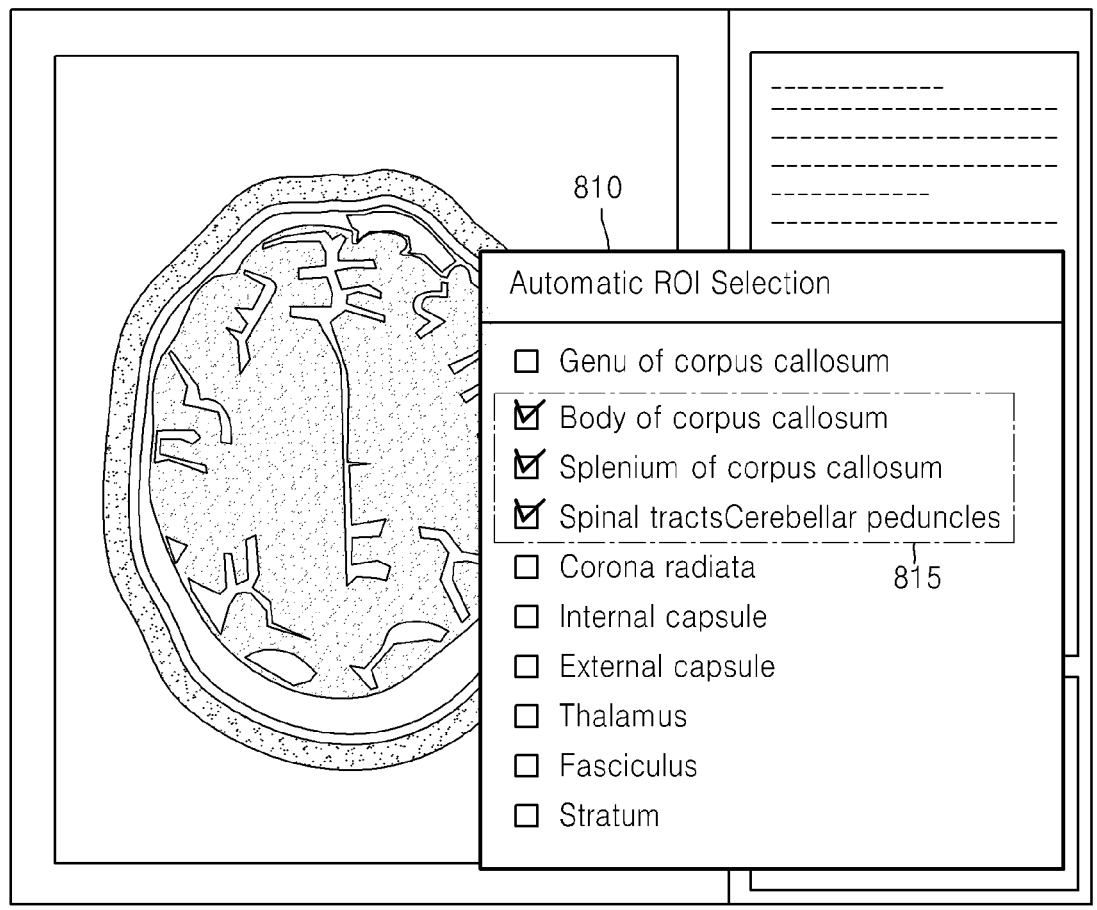
FIG. 8 illustrates an example of a screen which includes a brain area list which is displayed by an apparatus for selecting a seed area, according to an exemplary embodiment.

FIG. 8 illustrates an example of a screen which includes a brain area list which is displayed by the apparatus 100 for selecting a seed area, according to an exemplary embodiment. Referring to FIG. 8, the apparatus 100 for selecting a seed area according to the present exemplary embodiment may be configured to display, on the screen, a brain area list 810 based on the atlas which shows a plurality of areas of a brain.

The areas of a brain which are displayed on the brain area list 810 may include, for example, genu of corpus callosum, body of corpus callosum, splenium of corpus callosum, spinal tracts, cerebellar peduncles, corona radiata, internal capsule, external capsule, thalamus, fasciculus, and stratum. The brain area list 810 which is displayed by the apparatus 100 for selecting a seed area may include a plurality of buttons which correspond to the areas which are included in a brain. The user may select buttons 815 which respectively correspond to several areas that may be defined as seed areas.

The apparatus 100 for selecting a seed area may be configured to extract areas which correspond to selected buttons as seed areas based on a user input for selecting the buttons 815. The apparatus 100 for selecting a seed area may be configured to generate and display an image which shows a plurality of nerve fibers which pass through the seed areas extracted from the image data.

Figure 9:
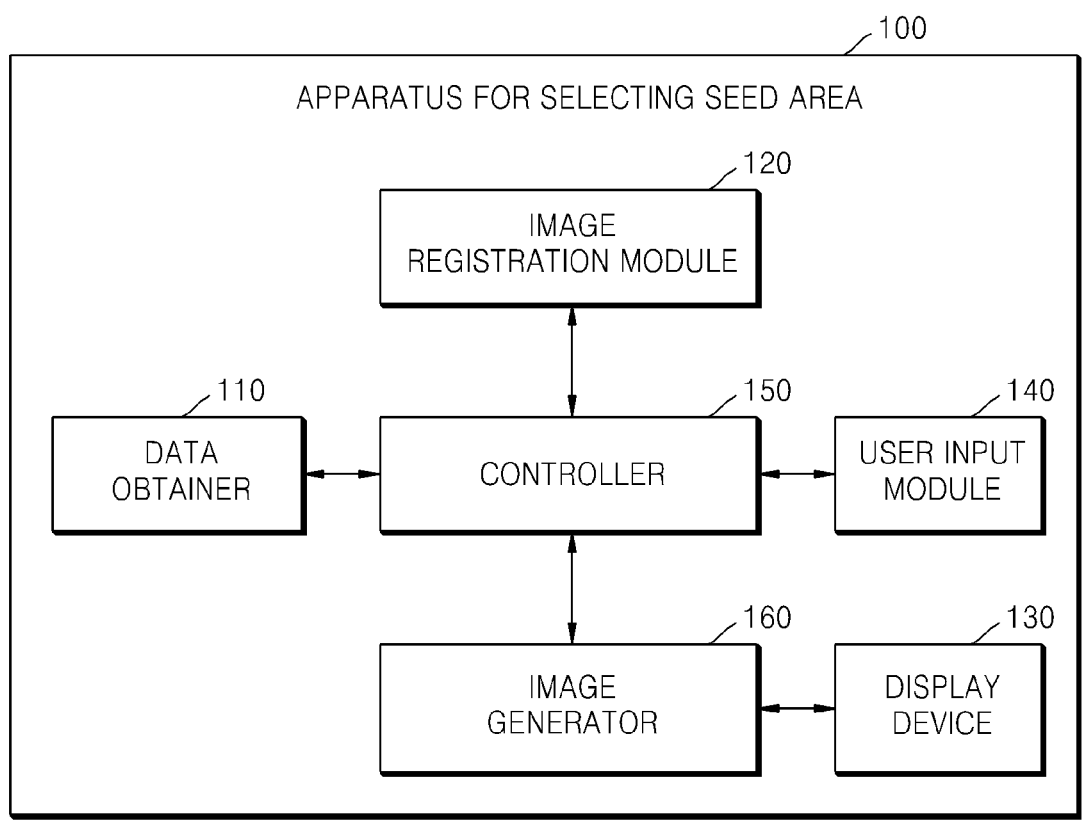
FIG. 9 is a block diagram which illustrates an apparatus for selecting a seed area, according to an exemplary embodiment.

FIG. 9 is a block diagram which illustrates the apparatus 100 for selecting a seed area, according to an exemplary embodiment. The constituent elements of the apparatus 100 for selecting a seed area according to the present exemplary embodiment are configured to perform each operation of the method for selecting a seed area which is illustrated in FIG. 2. Accordingly, the contents described above regarding the method for selecting a seed area of FIG. 2, although they are omitted in the following description, are applicable to the apparatus 100 for selecting a seed area which is illustrated in FIG. 9.

Referring to FIG. 9, the apparatus 100 for selecting a seed area according to the present exemplary embodiment may include a data obtaining unit (also referred to herein as a "data obtainer") 110, an image registration unit (also referred to herein as an "image registration module") 120, a display unit (also referred to herein as a "display device") 130, a user input unit (also referred to herein as a "user input module") 140, a control unit (also referred to herein as a "controller") 150, and an image generation unit (also referred to herein as an "image generator") 160. The apparatus 100 for selecting a seed area may be embodied in a variety of forms. For example, the apparatus 100 for selecting a seed area may be embodied not only as a fixed terminal but also as a mobile terminal. An example of a mobile terminal may include any one or more of laptop computers, personal digital assistants (PDAs), tablet PCs, etc.

In order for the apparatus 100 for selecting a seed area to track nerve fibers which are included in a brain, the data obtaining unit 110 may obtain an atlas which shows a plurality of areas which are included in the brain and image data which relates to the brain. The data obtaining unit 110 may receive an atlas from the outside or obtain an atlas which is previously stored in the apparatus 100 for selecting a seed area. The atlas which is obtained by the data obtaining unit 110 may include a brain area atlas which is formed based on the properties of nerve fibers of white matter.

Further, the data obtaining unit 110 may include an image capturing apparatus which is configured for obtaining image data from a brain. For example, the data obtaining unit 110 may include the MR image capturing apparatus 10 of FIG. 1. The data obtaining unit 110 may be configured to receive image data which is obtained by an image capturing apparatus separately from the apparatus 100 for selecting a seed area. For example, the data obtaining unit 110 may be configured to obtain MRI data from the MR image capturing apparatus 10. The data obtaining unit 110 may be configured to obtain a parameter which relates to a particular purpose, such as, for example, any one or more of an FA, a MD, and/or an ADC parameter from DTI data which is obtained by using a DTI pulse sequence.

The data obtaining unit 110 stores various pieces of information which are needed by the apparatus 100 for selecting a seed area in order to select a seed area. For example, the data obtaining unit 110 may be configured to store the atlas and the image data, but the present exemplary embodiment is not limited thereto.

The data obtaining unit 110 may include at least one of storage media such as flash memory, hard disks, multimedia cards (MMCs), card type memory, for example, secure digital (SD) memory or extreme digital (XD) memory, random access memory (RAM), static RAM, read-only memory (ROM), electrically erasable programmable read-only memory (EEPROM), programmable read-only memory (PROM), magnetic memory, magnetic disks, optical discs, etc. In addition, the data obtaining unit 110 may be configured to run a web storage or a cloud server that serves as a storage unit or a storage device.

The image registration unit 120 may be configured to perform a registration of the atlas which shows the areas which are included in a brain and the image data which relates to the brain.

The display unit 130 may be configured to display an image which is generated by the image generation unit 160. The display unit 130 may be configured to display a brain area list with respect to the areas of a brain which are shown by the atlas. In addition, the display unit 130 may be further configured to display a first image which corresponds to a seed area which is extracted by the control unit 150.

The display unit 130 may be configured to display information which is processed by the apparatus 100 for selecting a seed area. For example, the display unit 130 may be configured to display state information which is needed for obtaining the image data and for performing a registration of the image data with the atlas, a user interface (UI), and/or a graphic user interface (GUI) which relates to function settings and an image of a brain.

When a display panel and a touch pad that will be described below constitute a touch screen in a layer structure, the display unit 130 may be used as an input device in addition to being used as an output device. Examples of the display unit 130 may include at least one of a liquid crystal display (LCD), a thin film transistor-liquid crystal display (TFT-LCD), an organic light-emitting diode (OLED), a flexible display, a 3D display, and an electrophoretic display.

The user input unit 140 may receive a first user input with respect to the brain area list which is displayed via the display unit 130. The user input unit 140 may include any one or more of a keypad, a dome switch, a touch pad such as a capacitive overlay type, a resistive overlay type, an infrared beam type, a surface acoustic wave type, an integral strain gauge type, a piezoelectric effect type, etc., a jog wheel, a jog switch, and/or any other suitable type of input device, but the present exemplary embodiment is not limited thereto. In particular, when a touch pad forms a layer structure with a display panel as described above, the touch pad and display panel may collectively be referred to as a touch screen.

The control unit 150 may be configured to select a first area from the atlas based on the first user input. The control unit 150 may be configured to extract, as a seed area, an area of image data which corresponds to the selected first area, based on a result of a registration which is performed by the image registration unit 120. Further, the control unit 150 may control the overall operation of the apparatus 100 for selecting a seed area, and may control each of the data obtaining unit 110, the image registration unit 120, the display unit 130, the user input unit 140, and the image generation unit 160 in order to perform the method for selecting a seed area according to the present exemplary embodiment.

The image generation unit 160 may generate an image to be displayed on the display unit 130. For example, the image generation unit 160 may generate a first image which corresponds to a seed area from the image data.

As described above, according to the one or more of the above exemplary embodiments, nerve fibers may be easily and quickly tracked in that a user may use a single click to select a seed area, without wasting time on manually drawing a seed area on a sectional image of a brain. Further, according to the one or more of the above exemplary embodiments, the user may accurately select a desired area and reduce selection error by selecting a seed area based on a white matter atlas. Thus, according to the one or more of the above exemplary embodiments, misdiagnosis with regard to brain diseases and an error which might otherwise be generated during an operation may be reduced.

In addition, other exemplary embodiments can also be implemented by using computer readable code/instructions in/on a medium, e.g., a computer readable medium, in order to control at least one processing element to implement any above described exemplary embodiment. The medium can correspond to any transitory or non-transitory medium/media which permits the storage and/or transmission of the computer readable code.

The computer readable code can be recorded/transferred on a medium in a variety of ways, with examples of the medium including recording media, such as any one or more of magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure which includes or carries a signal or information, such as a device which carries a bitstream according to one or more exemplary embodiments. The medium may also include a distributed network, so that the computer readable code is stored/transferred and executed in a distributed fashion. Furthermore, the processing element could include a processor and/or a computer processor, and processing elements may be distributed and/or included in a single device. It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A method for selecting a seed area for tracking nerve fibers in a brain, the method comprising:
   performing a registration of an atlas which shows a plurality of areas which are included in the brain and image data which relates to the brain;
   displaying a brain area list with respect to the plurality of areas;
   selecting a first area from the atlas based on a first user input with respect to the brain area list;
   extracting, as the seed area, an area of the image data which corresponds to the first area, based on a result of the performing the registration; and
   generating a first image which corresponds to the seed area from the image data, and displaying the generated first image,
   wherein the generating and displaying the first image comprises:
   sequentially calculating a plurality of nerve fibers which pass through the seed area; and
   updating the first image based on a result of the calculating, wherein the first image includes image data which corresponds to at least one of the calculated plurality of nerve fibers.

2. The method of claim 1, wherein a plurality of nerve fibers which pass through the seed area are displayed in the first image.

3. The method of claim 1, wherein the atlas includes a white matter atlas.

4. The method of claim 1, wherein the image data includes magnetic resonance imaging (MRI) data which is obtainable by using a diffusion tensor imaging (DTI) technique.

5. The method of claim 1, wherein the performing the registration of the atlas comprises:
   obtaining a fractional anisotropy (FA) map from the image data; and
   performing a registration of the atlas and the obtained FA map.

6. The method of claim 1, further comprising:
   displaying a second image, which corresponds to the brain, and which is formed from the image data; and
   receiving a second user input with respect to the displayed second image,
   wherein the displaying the brain area list comprises generating and displaying the brain area list with respect to at least one area from among the plurality of areas, which at least one area relates to the received second user input.

7. The method of claim 1, further comprising:
   displaying a second image, which corresponds to the brain, and which is formed from the image data; and
   receiving a second user input with respect to the displayed second image,
   wherein the displaying the brain area list comprises generating and displaying the brain area list such that:

each of the plurality of areas is displayed in the second image; and at least one area from among the plurality of areas, which at least one area relates to the received second user input, is displayed to be different than other areas from among the plurality of areas.

8. The method of claim 1, further comprising:

displaying a second image, which corresponds to the brain, and which is formed from the image data;

receiving a second user input with respect to the brain area list; and displaying at least one area from among the plurality of areas, which displayed at least one area relates to the received second user input, to be different than other areas from among the plurality of areas.

9. An apparatus for selecting a seed area for tracking nerve fibers in a brain, the apparatus comprising:

a data obtainer which is configured for obtaining an atlas which shows a plurality of areas which are included in the brain and image data which relates to the brain;

an image registration module which is configured for performing a registration of the obtained atlas;

a display device which is configured for displaying a brain area list with respect to the plurality of areas;

a user input module which is configured for receiving a first user input with respect to the brain area list;

a controller which is configured for selecting a first area from the atlas based on the received first user input, and for extracting, as the seed area, an area of the image data which corresponds to the first area, based on a result of the performed registration; and an image generator which is configured for generating a first image which corresponds to the seed area from the image data, wherein the display device is further configured to display the generated first image, and wherein the image generator is further configured to sequentially calculate a plurality of nerve fibers which pass through the seed area and to update the first image based on a result of the calculation, wherein the first image includes image data which corresponds to at least one of the calculated plurality of nerve fibers, and wherein each of the image registration module, the controller and the image generator includes a processor.

10. The apparatus of claim 9, wherein a plurality of nerve fibers which pass through the seed area are displayed in the first image.

11. The apparatus of claim 9, wherein the atlas includes a white matter atlas.

12. The apparatus of claim 9, wherein the image data includes magnetic resonance imaging (MRI) data which is obtainable by using a diffusion tensor imaging (DTI) technique.

13. The apparatus of claim 9, wherein the image registration module is further configured to obtain a fractional anisotropy (FA) map from the image data and to perform a registration of the atlas and the FA map.

14. The apparatus of claim 9, wherein the image generator is further configured to generate a second image, which corresponds to the brain, and which is formed from the image data, the display device is further configured to display the generated second image, the user input module is further configured to receive a second user input with respect to the displayed second image, and the brain area list is generated and displayed with respect to at least one area from among the plurality of areas, which at least one area relates to the received second user input.

15. The apparatus of claim 9, wherein the image generator is further configured to generate a second image, which corresponds to the brain, and which is formed from the image data, the display device is further configured to display the generated second image, the user input module is further configured to receive a second user input with respect to the displayed second image, and the brain area list is generated and displayed such that:

each of the plurality of areas is displayed in the second image; and at least one area from among the plurality of areas, which at least one area relates to the received second user input, is displayed to be different than other areas from among the plurality of areas.

16. The apparatus of claim 9, wherein the image generator is further configured to generate a second image, which corresponds to the brain, and which is formed from the image data, the display device is further configured to display the generated second image, wherein each of the plurality of areas is displayed in the second image, the controller is further configured to receive a second user input with respect to the brain area list; and the display device is further configured to display at least one area from among the plurality of areas, which displayed at least one area relates to the received second user input, to be different than other areas from among the plurality of areas.

17. A non-transitory computer readable recording medium having recorded thereon a program, which, when executed by a computer, performs a method for selecting a seed area for tracking nerve fibers in a brain, the method comprising:

performing a registration of an atlas which shows a plurality of areas which are included in the brain and image data which relates to the brain;

displaying a brain area list with respect to the plurality of areas;

selecting a first area from the atlas based on a first user input with respect to the brain area list;

extracting, as the seed area, an area of the image data which corresponds to the first area, based on a result of the performing the registration; and generating a first image which corresponds to the seed area from the image data, and displaying the generated first image, wherein the generating and displaying the first image comprises:

sequentially calculating a plurality of nerve fibers which pass through the seed area; and updating the first image based on a result of the calculating, wherein the first image includes image data which corresponds to at least one of the calculated plurality of nerve fibers.

* * * * *